United States Patent [19]
Webb

[11] Patent Number: 5,836,309
[45] Date of Patent: Nov. 17, 1998

[54] BLOOD AND OTHER BODY FLUID CONTAINMENT TRAY

[76] Inventor: Nicholas J. Webb, 5370 Basel Dr., Wrightwood, Calif. 92397

[21] Appl. No.: 787,381

[22] Filed: Jan. 22, 1997

[51] Int. Cl.⁶ .................................................. A61G 15/00
[52] U.S. Cl. ........................... 128/845; 128/846; 128/857
[58] Field of Search ..................... 128/845, 846, 128/849–856; 604/317, 356; 5/636, 637, 638; 206/557; 220/571, 601, 661

[56] References Cited

U.S. PATENT DOCUMENTS

| | | | |
|---|---|---|---|
| 2,658,512 | 11/1953 | Tcheong | 128/292 |
| 2,751,268 | 6/1956 | Creelman | 311/5 |
| 4,736,736 | 4/1988 | Moers et al. | 128/75 |
| 5,048,136 | 9/1991 | Popitz | 5/431 |
| 5,195,538 | 3/1993 | Eldrige | 128/849 |
| 5,335,384 | 8/1994 | Foster et al. | 5/622 |
| 5,339,676 | 8/1994 | Johnson | 220/571 |
| 5,349,965 | 9/1994 | McCarver | 128/846 |
| 5,353,930 | 10/1994 | Berry | 206/557 |
| 5,415,180 | 5/1995 | Horan | 128/849 |
| 5,435,322 | 7/1995 | Marshall | 128/849 |
| 5,454,797 | 10/1995 | Haswell | 604/317 |
| 5,502,980 | 4/1996 | Faries | 128/849 |

*Primary Examiner*—Michael A. Brown
*Attorney, Agent, or Firm*—David P. Gordon

[57] ABSTRACT

A containment tray includes a contoured cradle having a floor surface and a drain portion, an entrance portion, a support portion situated between the entrance portion and the cradle, a raised rim, and a lower rim. The raised rim is provided around the cradle and support portion and provides splash protection from the fluids which drain into the cradle and a surface upon which a physician may stably rest his hands when performing surgery on a head or other body appendage held within the cradle. The lower rim provides stability for the containment tray as it rests on a surface. One preferred aspect of the containment tray is that the containment tray is made from a substantially transparent material, thereby not inhibiting the ability of a physician to view a wound or surgical site. Another preferred aspect is that the cradle is sloped toward the drain portion to facilitate drainage. A non-permeable closed cell foam may also be provided on the floor surface of the cradle.

20 Claims, 5 Drawing Sheets

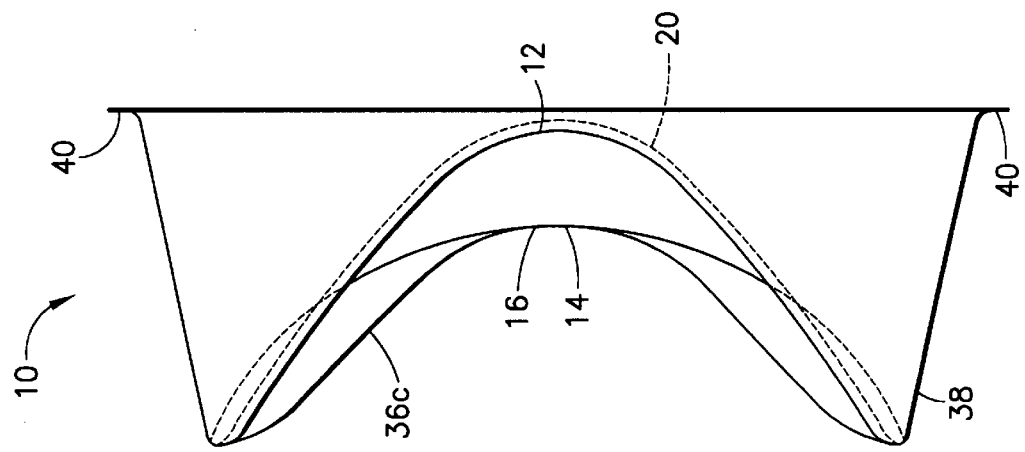
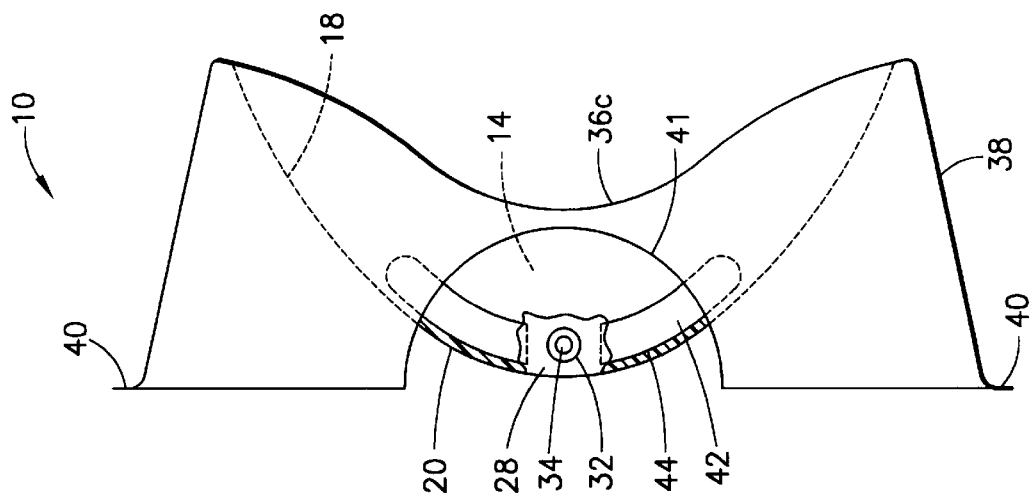

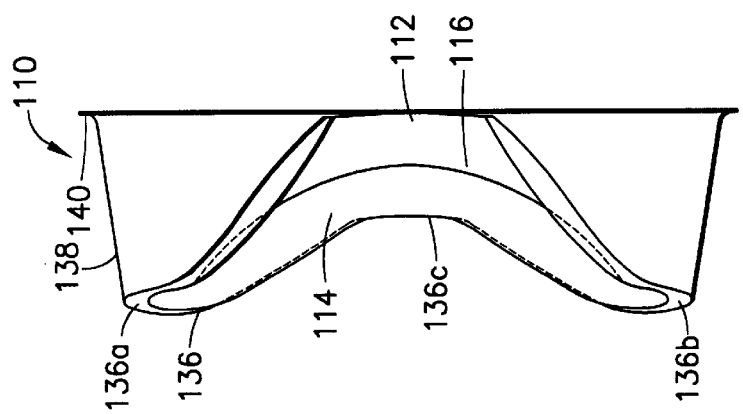
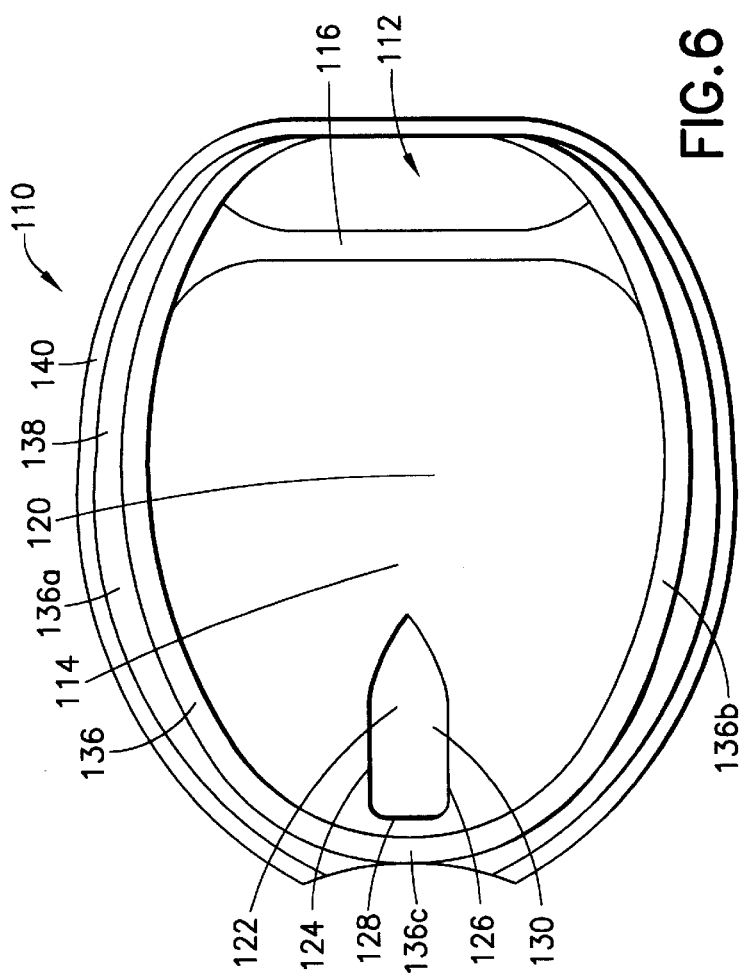
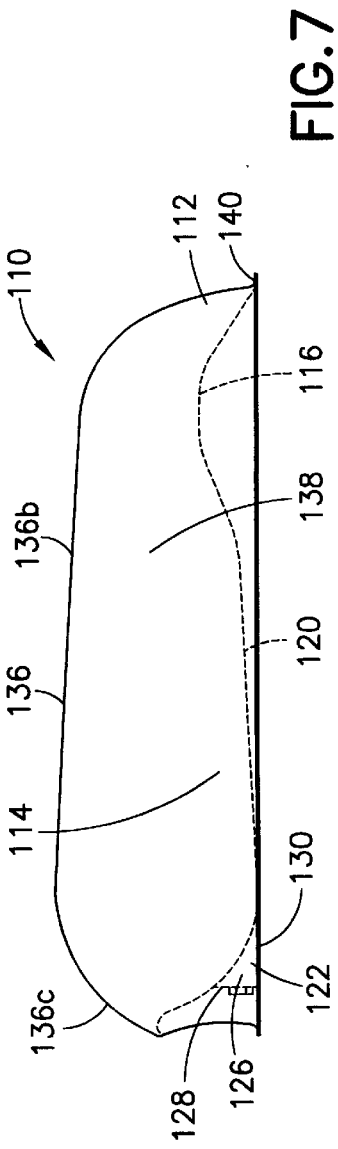

BLOOD AND OTHER BODY FLUID CONTAINMENT TRAY

BACKGROUND OF THE INVENTION

1. Field of the Invention

This invention relates broadly to a medical apparatus. More particularly, this invention relates to a containment tray which collects blood and other body fluids and provides support to a portion of the body from which blood and other body fluids are collected.

2. State of the Art

Emergency medical service teams commonly must attend to a trauma victim who has suffered a head injury. First contact with the trauma victim is often at the site of where the injury occurred. After administering critical assistance, the injured person is moved onto a gurney and attended to while being transported to a hospital where the trauma victim can receive more thorough care. From the moment the emergency medical services team arrives to care for the injured person to the time when the injured person is evaluated by a medical team at a hospital, usually no effort is made to contain and collect the body fluids, e.g., blood, exiting from the head of the trauma victim. Without collecting the fluids it is not readily ascertainable by an attending physician how much fluid has been lost from the trauma victim. In addition, without adequate means to collect the body fluids leaking from the head, a health threat is posed to those surrounding the trauma victim. For example, a serious concern is the threat of blood transmitted diseases, e.g., AIDS, hepatitis, etc. Without controlling the flow of the body fluids from the head, a level of safety for medical workers is lost. In addition, even if the body fluids exiting the head are contained, there exists a risk of spilling the fluids when the containment device is moved.

There is a similar need to control fluids exiting from the head or a body appendage during a surgical procedure. However, it is important that any containment device does not inhibit the ability of the physician to view the surgical area. Furthermore, it is important that such device have a shape which does not hinder the movement of the surgeon's hands around the surgical area. Moreover, it is desirable that such a device place the head or body appendage in a stable position.

SUMMARY OF THE INVENTION

It is therefore an object of the invention to provide a containment tray which collects body fluids exiting a portion of the body after injury or while undergoing a surgical procedure.

It is another object of the invention to provide a containment tray which cradles the head or a body appendage in a stable position.

It is an additional object of the invention to provide a containment tray which provides excellent visibility to the head or a body appendage cradled within the containment tray.

It is a further object of the invention to provide a containment tray which is designed to stabilize a physician's hands when examining or performing surgery.

It is also an object of the invention to provide a blood and fluid containment device which can receive the head or a body appendage.

It is yet another object of the invention to provide a containment tray which is stackable.

It is an additional object of the invention to provide a containment tray which is easy and inexpensive to manufacture.

In accord with these objects which will be discussed in detail below, a containment tray is provided. The containment tray broadly includes a contoured cradle having a floor surface and a drain, an entrance portion, and a support portion situated between the entrance portion and the cradle. The containment tray also preferably includes a raised rim from which the contoured cradle descends. The raised rim provides splash protection from the fluids which drain into the cradle and a surface upon which a surgeon may stably rest his or her hands when performing surgery on a head held within the cradle. A lower rim is also preferably included to provide stability for the containment tray as it rests on a surface.

There are several preferred aspect of the containment tray. One preferred aspect is that the containment tray is vacuum formed from a substantially transparent material permitting visualization to a person's head while attending a wound or when performing a medical procedure. Another preferred aspect is that the cradle is sloped toward the drain to facilitate drainage. Yet another preferred aspect is that the raised rim is curved to provided a generally rounded shape to the containment tray. It is also preferred that a non-permeable closed cell foam be provided on the floor surface of the cradle. The foam is a medical grade foam and is affixed to the floor surface with a medical grade adhesive.

The containment tray is described with respect to supporting a head and collecting fluids draining from the head, but can be used for supporting other body parts. For example, the containment tray can be used by a podiatrist while performing surgery on a foot or by a pediatrician for cradling a newborn.

Additional objects and advantages of the invention will become apparent to those skilled in the art upon reference to the detailed description taken in conjunction with the provided figures.

BRIEF DESCRIPTION OF THE DRAWINGS

FIG. 3 is a top end view of the containment tray of FIG. 1;

FIG. 4 is an entrance end view of the containment tray of FIG. 1;

FIG. 6 is a top view of a second embodiment of a containment tray according to the invention;

FIG. 7 is a side elevation view of the containment tray of FIG. 6;

FIG. 8 is an entrance end view of the containment tray of FIG. 6; and

DETAILED DESCRIPTION OF THE PREFERRED EMBODIMENTS

Figure 1:
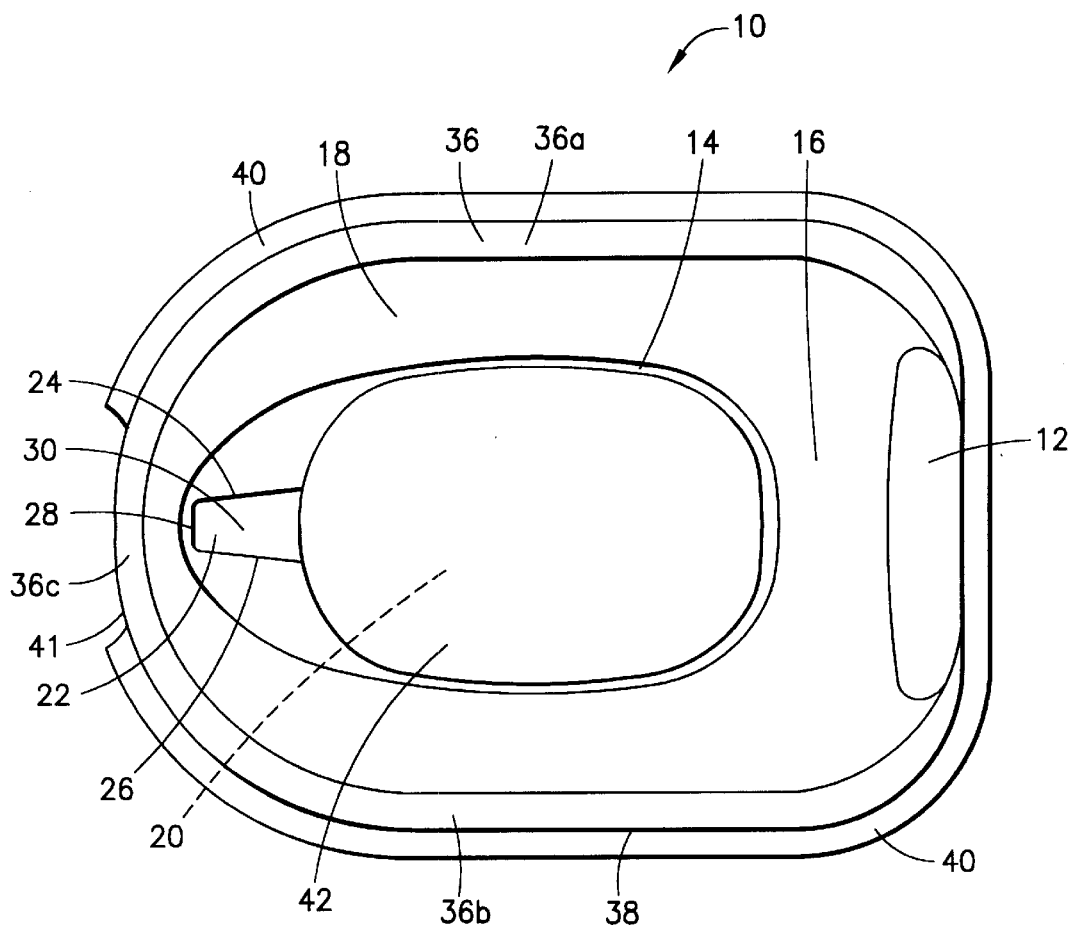
FIG. 1 is a top view of a first embodiment of a containment tray according to the invention.
Figure 2:
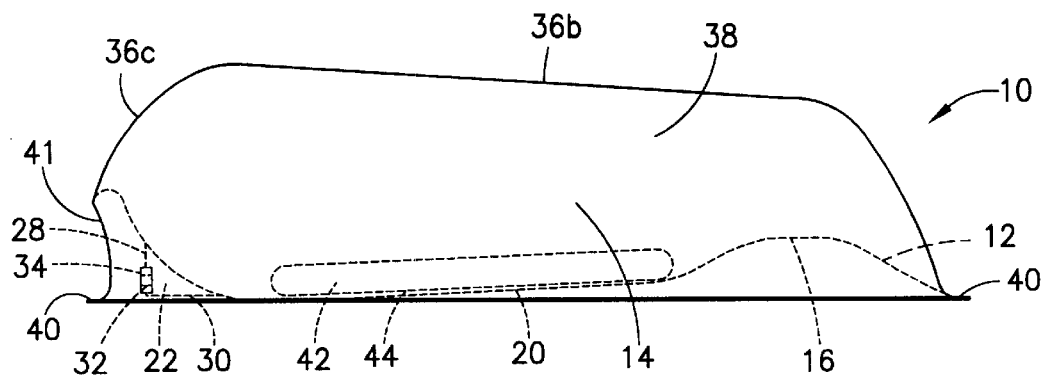
FIG. 2 is a side elevation view of the containment tray of FIG. 1.
Figure 5:
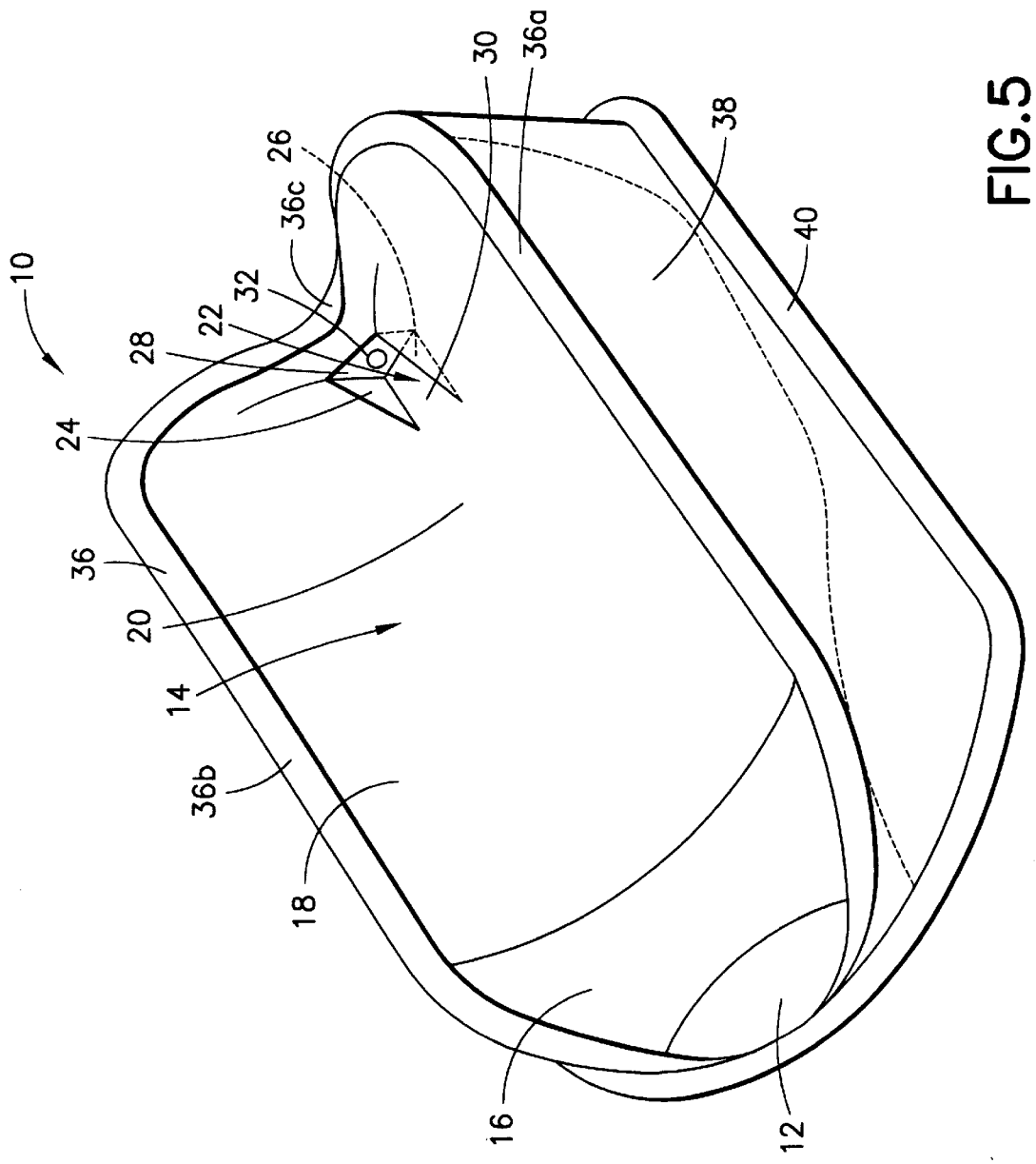
FIG. 5 is a perspective view of the containment tray of FIG. 1.

Turning now to FIGS. 1 through 5, a containment tray 10 according to a first embodiment of the invention is shown. The containment tray 10 generally includes an entrance portion 12, a cradle 14, and a support portion 16 located between the entrance portion 12 and the cradle 14. The entrance portion 12 is preferably designed to permit the head and neck of person to extend into the containment tray. The support portion 16 curves up from the entrance portion 12 before curving back down into the cradle 14 and is preferably designed to support the neck of person such that the head comfortably rests in the cradle. The cradle 14 has a gradually downward sloping interior wall 18 which slopes to form a floor surface 20. The floor surface 20 is preferably sloped downward away from the support portion 16, and preferably a drain portion 22 is provided at the lowest area of the floor surface 20.

The drain portion 22 has two side walls 24, 26, an outlet wall 28, and a lower drain surface 30 which is located between the two side walls 24, 26 and the outlet wall 28. The outlet wall 28 is preferably provided with a drain hole 32 and a removable plug 34 extending through the drain hole. The removable plug 34 gives the user the option of self-containing fluids within the tray, or removing the plug 34 prior to usage for connection to an external suction source. Alternatively, no drain hole is provided and the outlet wall is adapted to be later perforated to thereby form a drain hole. With either alternative, it will be appreciated that the containment tray is stackable, permitting a large number of containment trays to be stored in a relatively small space.

A raised rim 36 is provided around the cradle 14 and the support portion 16. The raised rim 36 provides a splash guard from fluids collected in the cradle 14 and also provides a surface upon which a surgeon can rest and stabilize his or her hands during a surgical procedure or during an examination. The raised rim 36 includes relatively higher lateral portions 36a, 36b and a downward curving top portion 36c, which facilitates access to the top of a head situated in the cradle 14.

On the outside of the raised rim 36, an outside wall 38 slopes steeply downward and curves or bends sharply to form a substantially horizontal lower rim 40. The lower rim 40 stably supports the containment tray 10 on a relatively flat surface. Near the top portion 36c of the rim 36, the outside wall 38 is provided with a cutout 41 which provides access to the drain portion 22.

Preferably the containment tray is vacuum formed from a substantially transparent, inexpensive, and lightweight material, e.g., a thermoplastic such as polyethylene. The substantially transparent quality of the material provides at least three benefits. First, a physician is better able to superficially ascertain the condition of injuries on a trauma victim's head held within the containment tray by simply viewing the head through the substantially transparent exterior and interior walls 18, 38. Second, prior to draining the cradle 14, a physician is able to ascertain the quantity of fluid lost by the trauma victim which is contained in the containment tray. Third, a surgeon has greater visibility of the head during a surgical procedure. In addition, it is preferable that the containment tray be tinted green or blue in order to reduce the visual impact of blood.

It is also preferable to provide a foam cushioning 42 on the floor surface 20. Preferably, the foam cushioning 42 is a medical grade non-permeable closed cell foam and is affixed to the floor surface 20 with a medical grade adhesive 44, e.g., medical grade tape or glue.

By way of example, the following dimensions represent one implementation of the first embodiment of the containment tray. The containment tray 10 is approximately twelve inches wide and seventeen inches in length. The raised and lower rims 36, 40 are approximately ⅝ inches wide, and the raised rim 36 is located approximately four inches above the lower rim 40. The exterior wall 38 between the raised rim 36 and the lower rim 40 slopes downward at approximately a 75°–85° angle. The raised rim 36 curves downward at approximately a 55° angle to provide the entrance portion 12. The support portion 16 is approximately four and a half inches wide and is formed by an upward curve which rises approximately one inch from the entrance portion 12 and then curves back down to the cradle 14, and is further formed by a downward curve which descends approximately two and a quarter inches from the raised rim 36. The cradle 14 is approximately eight inches wide, nine inches in length, and at the lateral midpoint of the width of the cradle 14 the depth relative to the lateral portions 36a, 36b of the raised rim ranges from approximately three inches, at the highest point of the sloped floor surface 20, to approximately four inches, at the lowest point of the sloped floor surface. The top portion 36c of the raised rim curves downward at approximately a 40° angle, at its lowest point being approximately two inches above the floor surface 20 and approximately two inches below the lateral portions 36a, 36b of the raised rim 36. The drain portion 22 is provided in the cradle 14 at the lowest point of the sloped floor surface 20 and adjacent the lowest portion of the top portion 36c of the raised rim 36. The outlet wall 28 of the drain portion 22 is approximately one inch in height and one and a quarter inches wide. The lower drain surface 30 is approximately one and a quarter inches wide and one and a half inches in length.

Figure 9:
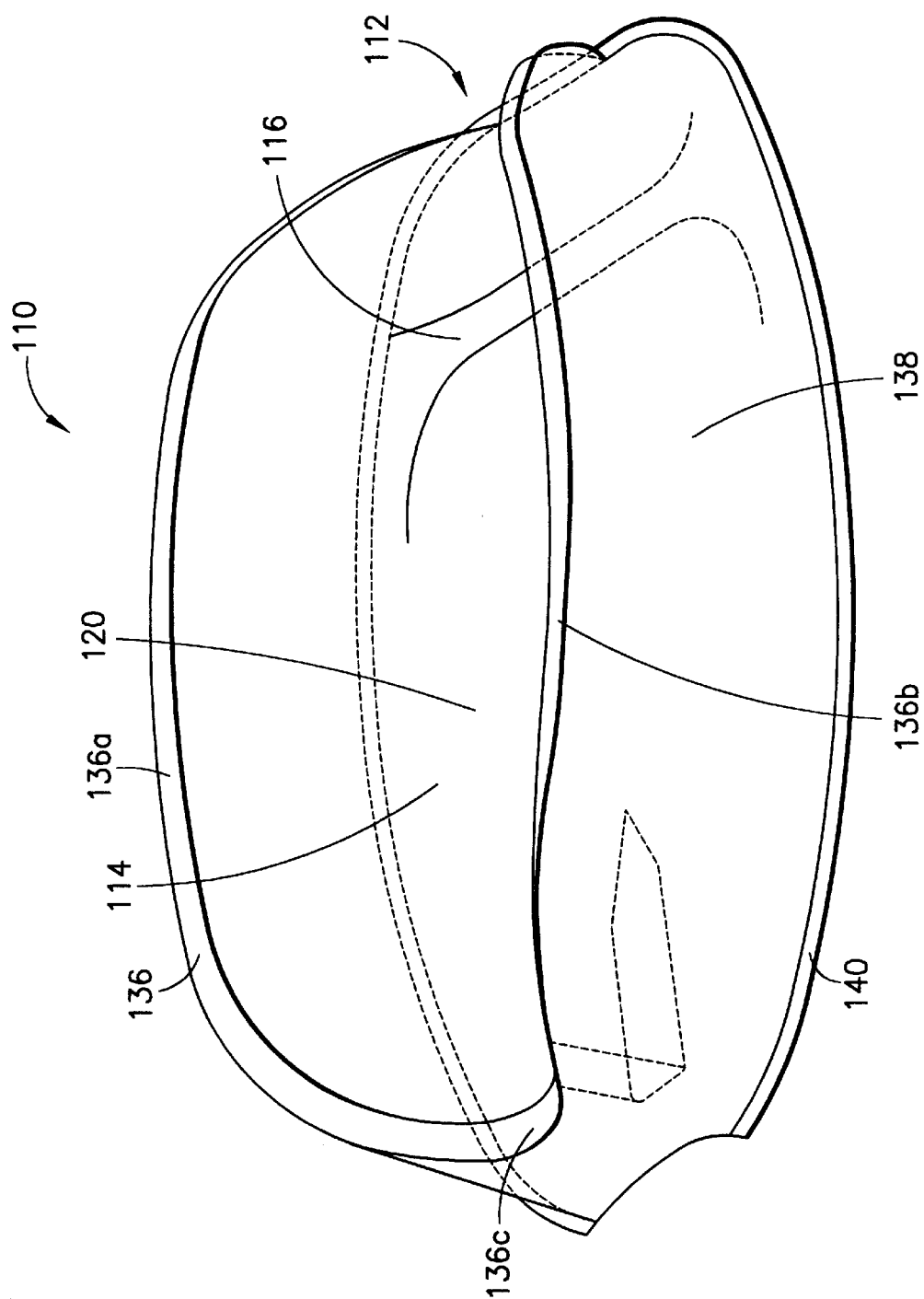
FIG. 9 is a perspective view of the containment tray of FIG. 6.

A preferred second embodiment of a containment tray, substantially similar to the first embodiment (with like parts having numbers incremented by 100), is shown in FIGS. 6 through 9. The containment tray 110 generally includes an entrance portion 112, a cradle 114, and a support portion 116 located between the entrance portion 112 and the cradle 114. The cradle 114 has a floor surface 120. The floor surface 120 is preferably sloped downward away from the support portion 116, and preferably a drain portion 122 is provided at the lowest area of the floor surface 120. The drain portion 122 has two side walls 124, 126, an outlet wall 128, and a lower drain surface 130 which is located between the two side walls 124, 126 and the outlet wall 128. A curved raised rim 136 is provided around the cradle 114 and the support portion 116, thereby giving the containment tray 110 a generally rounded shape. The raised rim 136 slopes downward from the cradle 114 to the support portion 116. The raised rim 136 includes relatively higher lateral portions 136a, 136b and a downward curving top portion 136c. On the outside of the raised rim 136, an outside wall 138 slopes steeply downward and curves or bends sharply to form a substantially horizontal lower rim 140.

By way of further example, the following dimensions are for one implementation of the preferred second embodiment of the containment tray 110 of the invention. The containment tray 110 is approximately thirteen inches wide and fifteen and one half inches in length. The raised rim 136 is approximately one half inch wide, and the lower rim 140 is approximately one quarter inch wide. The raised rim 136 ranges from between approximately four and 3.4 inches above the lower rim 140, sloping gently downward from the cradle 114 to the support portion 116. The exterior wall 138 between the raised rim 136 and the lower rim 140 slopes downward at approximately 80°. The raised rim 136 curves downward at approximately a 45° angle to provide the entrance portion 112. The support portion 116 is approximately four inches wide and rises approximately 1 inch above the lower rim 140. The cradle 114 is approximately ten inches wide at its widest point, approximately nine inches in length, and at the lateral midpoint of the width of the cradle 114 the depth relative to the lateral portions 136*a*, 136*b* of the raised rim ranges from approximately three inches, at the highest point of the sloped floor surface 120, to approximately four inches, at the lowest point of the sloped floor surface. The top portion 136*c* of the raised rim curves downward at approximately a 45° angle, its lowest point being approximately two inches above the floor surface 120 and approximately two inches below the lateral portions 136*a*, 136*b* of the rim 136. The drain portion 122 is provided in the cradle 114 at the lowest point of the sloped floor surface 120 and adjacent the lowest portion of the top portion 136*c* of the raised rim 136. The outlet wall 128 of the drain portion 122 is approximately one inch in height and one and a quarter inches wide. The lower drain surface 130 is approximately one and a third inches wide and one and a half inches in length.

There has been described and illustrated herein body fluid containment trays. While particular embodiments of the invention have been described, it is not intended that the invention be limited thereto, as it is intended that the invention be as broad in scope as the art will allow and that the specification be read likewise. Thus, while the preferred material of the containment tray has been disclosed as substantially transparent, it will be appreciated that substantially opaque materials may be used as well. In addition, while a luer connector has been disclosed for coupling a drainage tube thereto, it will be understood that other couplings may be used. Furthermore, while a drain has been disclosed as preferred, it will be appreciated that a drain may be undesirable for some applications, and that a drain need not be provided. Moreover, while particular dimensions have been disclosed, other dimensions could be used, particularly for trays intended for children. In addition, while the containment trays were described with respect to supporting a head and collecting fluids draining from the head, it will be appreciated that the containment trays can be adapted for use with other body parts, and may be useful in pediatric and podiatry applications among others. It will therefore be appreciated by those skilled in the art that yet other modifications could be made to the provided invention without deviating from its spirit and scope as so claimed.

What is claimed is:

1. A containment tray, comprising:
   a) an upper rim having an opening defining an entrance portion; and
   b) an interior surface, sloping downward from said upper rim to form a cradle, and curving upward between said cradle and said entrance portion to form a support portion, said cradle having a floor surface and a drain portion, said drain portion adapted to receive a drain, and said floor surface sloping downward from said support portion to said drain portion.

2. A containment tray according to claim 1, wherein:
   said upper rim has a lower curving portion where said upper rim is closest to said drain portion.

3. A containment tray according to claim 1, wherein:
   said containment tray is made from a substantially transparent material.

4. A containment tray according to claim 1, wherein:
   said upper rim and said interior surface are made from a unitary piece of a thermoplastic.

5. A containment tray according to claim 1, further comprising:
   c) an outside wall extending downward from said upper rim; and
   d) a substantially horizontal lower rim extending around said outside wall and said entrance portion.

6. A containment tray according to claim 1, further comprising:
   e) a non-permeable closed cell medical grade foam provided on said floor surface.

7. A containment tray according to claim 1, wherein:
   said containment trays are stackable.

8. A containment tray, comprising:
   a) an upper rim having an opening defining an entrance portion; and
   b) an interior surface, sloping downward from said upper rim to form a cradle, and curving upward between said cradle and said entrance portion to form a support portion,
   wherein said containment tray is made from a substantially transparent material.

9. A containment tray according to claim 8, wherein:
   said upper rim and said interior surface are made from a unitary piece of a thermoplastic.

10. A containment tray according to claim 8, further comprising:
    c) an outside wall extending downward from said upper rim; and
    d) a substantially horizontal lower rim extending around said outside wall and said entrance portion.

11. A containment tray according to claim 8, further comprising:
    e) a non-permeable closed cell medical grade foam provided on said floor surface.

12. A containment tray, comprising:
    a) a cradle adapted to receive the head of a person, said cradle having a floor surface and a drain portion, said drain portion adapted to receive a drain;
    b) an entrance portion adapted to receive the neck of a person; and
    c) a curved support portion adapted to support the neck of a person, said support portion situated between said entrance portion and said cradle,
    wherein said floor surface slopes downward from said support portion to said drain portion.

13. A containment tray according to claim 12, further comprising:
    d) an upper rim located around said cradle and said support portion.

14. A containment tray according to claim 13, wherein:
    said upper rim has a lower curving portion where said upper rim is closest to said drain portion.

15. A containment tray according to claim 13, wherein:
    said cradle, said floor, said drain portion, said entrance portion, said support portion, and said upper rim are formed from a unitary piece of thermoplastic.

16. A containment tray according to claim 13, further comprising:
    e) an outside wall extending downward from said upper rim; and
    f) a substantially horizontal lower rim extending around said outside wall and said entrance portion.

17. A containment tray according to claim 12, further comprising:

g) a non-permeable closed cell medical grade foam provided on said floor surface.

18. A containment tray, comprising:

a) a cradle adapted to receive the head of a person;

b) an entrance portion adapted to receive the neck of a person; and c) a curved support portion adapted to support the neck of a person, said support portion situated between said entrance portion and said cradle, wherein said containment tray is made from a substantially transparent material.

19. A containment tray according to claim 18, wherein:

said cradle, said entrance portion, and said support portion are formed from a unitary piece of thermoplastic.

20. A containment tray according to claim 19, further comprising:

d) an upper rim located around said cradle and said support portion;

e) an outside wall extending downward from said upper rim; and f) a substantially horizontal lower rim extending around said outside wall and said entrance portion.

* * * * *